(12) United States Patent
Huang et al.

(10) Patent No.: US 8,741,588 B2
(45) Date of Patent: Jun. 3, 2014

(54) MONOCLONAL ANTIBODIES AGAINST PBP2A DERIVED FROM MRSA AND METHODS OF USE

(75) Inventors: Ruo-Pan Huang, Johns Creek, GA (US); Ying Zhang, Johns Creek, GA (US)

(73) Assignee: Raybiotech, Inc., Norcross, GA (US)

( * ) Notice: Subject to any disclaimer, the term of this patent is extended or adjusted under 35 U.S.C. 154(b) by 0 days.

(21) Appl. No.: 13/555,290

(22) Filed: Jul. 23, 2012

(65) Prior Publication Data
US 2013/0022997 A1    Jan. 24, 2013

Related U.S. Application Data

(60) Provisional application No. 61/510,111, filed on Jul. 21, 2011.

(51) Int. Cl.
*C07K 16/12*    (2006.01)
*C07K 14/31*    (2006.01)
*G01N 33/577*   (2006.01)

(52) U.S. Cl.
USPC ........... 435/7.33; 435/7.1; 435/7.2; 435/7.32; 530/350; 530/387.9; 530/326; 530/324

(58) Field of Classification Search
None
See application file for complete search history.

(56) References Cited

PUBLICATIONS

Skolnick et al. (Trends in Biotechnology 18: 34-39, 2000).*
Greenspan et al. (Nature Biotechnology 7: 936-937, 1999).*
Bowie et al (Science, 1990, 257:1306-1310—IDS filed on Aug. 30, 2012).*

* cited by examiner

*Primary Examiner* — Robert A Zeman
(74) *Attorney, Agent, or Firm* — Thomas|Horstemeyer, LLP

(57) ABSTRACT

Mouse monoclonal antibodies specifically recognizing the Penicillin Binding Protein 2a (PBP2a) derived from a strain of Methicillin-Resistant *Staphylococcus aureus* (MRSA) were produced and characterized. The immunogen used to generate an immune response in a mouse was a PBP2a recombinant protein derived from a strain of Methicillin-Resistant *Staphylococcus aureus* (MRSA). The data showed that both monoclonal antibodies of the disclosure were able to distinguish MRSA from MSSA bacteria. The monoclonal antibodies have distinct recognition patterns for the regions of the PBP2a protein sequence. Epitope mapping has localized regions of the PBP2a protein specifically recognized by one or both of the monoclonal antibodies. The monoclonal antibodies of the present disclosure having the ability to distinguish between MRSA and MSSA strains can be useful as the basis for a diagnostic assay useful in the clinical setting for determining whether and which antibiotics to administer to a patient.

6 Claims, 9 Drawing Sheets

50KDa

SEQ ID No.: 14

```
          10         20         30         40         50         60
MKKIKIVPLI LIVVVVGFGI YFYASKDKEI NNTIDAIEDK NFKQVYKDSS YISKSDNGEV 70         80         90        100        110        120
EMTERPIKIY NSLGVKDINI QDRKIKKVSK NKKRVDAQYK IKTNYGNIDR NVQFNFVKED 130        140        150        160        170        180
GMWKLDWDHS VIIPGMQKDQ SIHIENLKSE RGKILDRNNV ELANTGTAYE IGIVPKNVSK 190        200        210        220        230        240
KDYKAIAKEL SISEDYIKQQ MDQNWVQDDT FVPLKTVKKM DEYLSDFAKK FHLTTNETES 250        260        270        280        290        300
RNYPLGKATS HLLGYVGPIN SEELKQKEYK GYKDDAVIGK KGLEKLYDKK LQHEDGYRVT 310        320        330        340        350        360
IVDDNSNTIA HTLIEKKKKD GKDIQLTIDA KVQKSIYNNM KNDYGSGTAI HPQTGELLAL 370        380        390        400        410        420
VSTPSYDVYP FMYGMSNEEY NKLTEDKKEP LLNKFQITTS PGSTQKILTA MIGLNNKTLD 430        440        450        460        470        480
DKTSYKIDGK GWQKDKSWGG YNVTRYEVVN GNIDLKQAIE SSDNIFFARV ALELGSKKFE 490        500        510        520        530        540
KGMKKLGVGE DIPSDYPFYN AQISNKNLDN EILLADSGYG QGEILINPVQ ILSIYSALEN 550        560        570        580        590        600
NGNINAPHLL KDTKNKVWKK NIISKENINL LTDGMQQVVN KTHKEDIYRS YANLIGKSGT 610        620        630        640        650        660
AELKMKQGET GRQIGWFISY DKDNPNMMMA INVKDVQDKG MASYNAKISG KVYDELYENG

NKKYDIDE
```

*Fig. 8*

Anti-PBP2a monoclonal antibody

*Antigen:1734*

1  MKKIKIVPLILIVVVVGFGI (SEQ ID No.: 3)

2  VGFGIYFYASKDKEINNTID (SEQ ID No.: 4)

3  NNTIDAIEDKNFKQVYKDSS (SEQ ID No.: 5)

4  YKDSSYISKSDNGEVEMTER (SEQ ID No.: 6)

Fine Epitope: NNTIDAI*EDK*NFKQV (SEQ ID No.: 7)

Anti-MRSA monoclonal antibody

*Antigen:1733*

25  VSTPSYDVYPFMYGMSNEEY (SEQ ID No.: 8)

26  SNEEYNKLTEDKKEPLLNKF (SEQ ID No.: 9)

27  LLNKFQITTSPGSTQKILTA (SEQ ID No.: 10)

28  KILTAMIGLNNKTLDDKTSY (SEQ ID No.: 11)

29  Fine Epitope: SNEEYNKLT*EDK*KEP (SEQ ID No.: 12)

Both epitopes contain the critical motif:

NX  TX  EDK  XKX (SEQ ID No.: 13

*Fig. 9*

MONOCLONAL ANTIBODIES AGAINST PBP2A DERIVED FROM MRSA AND METHODS OF USE

CROSS-REFERENCE TO RELATED APPLICATIONS

This application claims priority to U.S. Provisional Patent Application Ser. No. 61/510,111 entitled "MONOCLONAL ANTIBODY AGAINST PBP2A DERIVED FROM MRSA WITH DUAL BINDING ACTIVITIES" and filed Jul. 21, 2011, the entirety of which is hereby incorporated by reference.

SEQUENCE LISTING

The present disclosure includes a sequence listing incorporated herein by reference in its entirety.

TECHNICAL FIELD

The present disclosure is generally related to monoclonal antibodies specific for an epitope of Methicillin-sensitive *Staphylococcus aureus* (MRSA) and to methods of distinguishing MRSA from MSSA strains.

BACKGROUND

Methicillin-Resistant *Staphylococcus aureus* (MRSA) is a major pathogen responsible for serious hospital infections worldwide. These bacteria are resistant to all β-lactam antibiotics due to the production of an additional penicillin-binding protein, the PBP2a (about 75 kDa) encoded by the mecA gene, and which shows low affinity for this class of antibiotics. The protein is the target of lactam antibiotics. The two main groups of *Staphylococcus aureus* are classified as MRSA and MSSA (Methicillin-sensitive *Staphylococcus aureus*) depending on whether they are resistant or sensitive to antibiotics.

SUMMARY

Briefly described, one aspect of the disclosure encompasses embodiments of a monoclonal antibody characterized as specifically binding to an epitope of a methicillin-resistant strain of *Staphylococcus aureus* and not binding to an epitope of a methicillin-sensitive strain of *Staphylococcus aureus*.

In the embodiments of this aspect of the disclosure, the monoclonal antibody of is characterized as selectively binding to at least one epitope of a *S. aureus* PBP2a protein having the amino acid sequence SEQ ID No.: 14.

In the embodiments of this aspect of the disclosure, the monoclonal antibody of is characterized as selectively binding to an epitope located in a region between amino acid positions of about 27 to about 46 of the PBP2a protein sequence SEQ ID No.: 14 that consists essentially of the amino acid sequence DKEINNTIDAIEDKNFKQVY (SEQ ID No.: 1).

In the embodiments of this aspect of the disclosure, the monoclonal antibody of is characterized as selectively binding to an epitope located in a region between amino acid positions of about 27 to about 46 of the PBP2a protein sequence SEQ ID No.: 14 that consists essentially of the amino acid sequence DKEINNTIDAIEDKNFKQVY (SEQ ID No.: 1) and as selectively binding to an epitope located in a, the region between amino acid positions of about 375 to about 400 of the PBP2a protein sequence SEQ ID No.: 14 that consists essentially of the amino acid sequence SNEEYNKLTEDKKEPLLNKFQITTS (SEQ ID No.: 2). In the embodiments of this aspect of the disclosure, the monoclonal antibody can have the designation 10A10.F2.

In the embodiments of this aspect of the disclosure, the monoclonal antibody can have the designation 4B10.B6 and is produced by the hybridoma deposited with the American Type Culture Collection and having the ATCC Patent Deposit Designation PTA-12026.

In the embodiments of this aspect of the disclosure, the monoclonal antibody can have the designation 20G10H8 and is produced by the hybridoma deposited with the American Type Culture Collection and having the ATCC Patent Deposit Designation PTA-12027.

Another aspect of the disclosure encompasses embodiments of an epitope of a PBP2a protein isolated from a methicillin-resistant strain of *Staphylococcus aureus*, where the epitope can selectively react with a monoclonal antibody characterized as distinguishing a methicillin-resistant strain of *Staphylococcus aureus* from a methicillin-sensitive strain of *Staphylococcus aureus*.

In the embodiments of this aspect of the disclosure, the epitope can be isolated from between the amino acid positions of about 27 to about 46 and having the amino acid sequence DKEINNTIDAIEDKNFKQVY (SEQ ID No.: 1), or between amino acid positions of about 375 to about 400 and having the amino acid sequence SNEEYNKLTEDKKEPLLNKFQITTS (SEQ ID No.: 2) of the *S. aureus* PBP2a protein, and wherein the epitope comprises the amino acid motif EDK In the embodiments of this aspect of the disclosure, the epitope can be specifically recognized by the monoclonal antibody 4B10.B6 produced by the hybridoma deposited with the American Type Culture Collection and having the ATCC Patent Deposit Designation PTA-12026.

In the embodiments of this aspect of the disclosure, the epitope can be specifically recognized by monoclonal antibody 10A10.F2.

In the embodiments of this aspect of the disclosure, the epitope can be specifically recognized by monoclonal antibody 20G10H8 produced by the hybridoma deposited with the American Type Culture Collection and having the ATCC Patent Deposit Designation PTA-12027.

Yet another aspect of the present disclosure encompasses embodiments of a method of differentiating a methicillin-resistant strain of *Staphylococcus aureus* from a methicillin-sensitive strain of *Staphylococcus aureus*, comprising the steps of: (i) obtaining a biological sample suspected of comprising a strain of *Staphylococcus;* (ii) providing a detection system by contacting the biological sample with at least one capture monoclonal antibody characterized as having specific affinity for an epitope of a PBP2a protein isolated from a methicillin-resistant strain of *Staphylococcus aureus*, wherein the monoclonal antibody is further characterized as distinguishing a methicillin-resistant strain of *Staphylococcus aureus* from a methicillin-sensitive strain of *Staphylococcus aureus;* and (iii) detecting the binding of the at least one capture monoclonal antibody to the biological sample, thereby detecting a population of methicillin-resistant *S. aureus* in the biological sample.

In the embodiments of this aspect of the disclosure, the at least one capture monoclonal antibody can be bound to a solid support.

In the embodiments of this aspect of the disclosure, the at least one capture monoclonal antibody can be selected from the group consisting of the monoclonal antibodies designated: 4B10.B6 having the ATCC Patent Deposit Designation PTA-12026, 10A10.F2, and 20G10H8 having the ATCC Patent Deposit Designation PTA-12027.

In the embodiments of this aspect of the disclosure, the at least one capture monoclonal antibody can be antibody 4B10.B6 having the ATCC Patent Deposit Designation PTA-12026.

In the embodiments of this aspect of the disclosure, the at least one capture monoclonal antibody can be antibody 10A10.F2.

In the embodiments of this aspect of the disclosure, the at least one capture monoclonal antibody is antibody 20G10H8 having the ATCC Patent Deposit Designation PTA-12027.

In the embodiments of this aspect of the disclosure, the at least one capture monoclonal antibody can be a combination of monoclonal antibody designated: 4B10.B6 having the ATCC Patent Deposit Designation PTA-12026 and monoclonal antibody 20G10H8 having the ATCC Patent Deposit Designation PTA-12027.

In the embodiments of this aspect of the disclosure, the step (iii) can comprise contacting the detection system with a second antibody, where the second antibody is detectably labeled and characterized as specifically binding to a PBP2a epitope bound to the at least one capture monoclonal antibody.

BRIEF DESCRIPTION OF THE DRAWINGS

Further aspects of the present disclosure will be more readily appreciated upon review of the detailed description of its various embodiments, described below, when taken in conjunction with the accompanying drawings.

FIG. 2A illustrates the binding of an MRSA-specific monoclonal antibody of the disclosure. Sample loading of a 12% SDS-PAGE gel: 1: Marker; 2: PBP2a (2 μg/lane); and 3: MR1 (15 μL/lane).

FIG. 2B illustrates the binding of a PBP2a-specific monoclonal antibody of the disclosure. Sample loading of a 12% SDS-PAGE gel: 1: PBP2a (2 μg/lane); 2: PBP2a (0.2 μg/Lane), and 3: MR1 (15 μL/each lane).

FIG. 6A: 4B10.B6 clone (isotype IgG1); FIG. 6B: 10A10 clone (isotype IgM); FIG. 6C: commercial anti-MRSA mAb; FIG. 6D: commercial anti-PBP2a mAb. Loading: 1: Marker; 2: MRSA; 3: MSSA; 4: SEP1; 5: *E. coli*-HE4.

FIG. 7A: Staining Gel; FIG. 7B: Specific detection. Pulled down assay: pre-incubated MRSA bacterial sample with 4B10.B6 antibody, then further incubated with anti-mouse-beads; the eluted complexes from the beads were loaded onto SDS-PAGE gel, the membrane blotting was probed by biotinylated 10A10.F2 antibody, and finally detected by Streptavidin-HRP. Loading: Lane 1: Marker; Lane 2: MRSA sample+precipitated antibody (15 μL/lane); Lane 3: MSSA sample+precipitated antibody (15 μL/lane).

FIG. 8 illustrates the amino acid sequence of PBP2a (SEQ ID No.: 14). Regions used to identify the epitope recognized by the monoclonal antibodies of the disclosure are underlined.

FIG. 9 illustrates the binding sites (SEQ ID Nos.: 3-7 and 8-12) of the two antibodies of the disclosure to MRSA.

Figure 1:
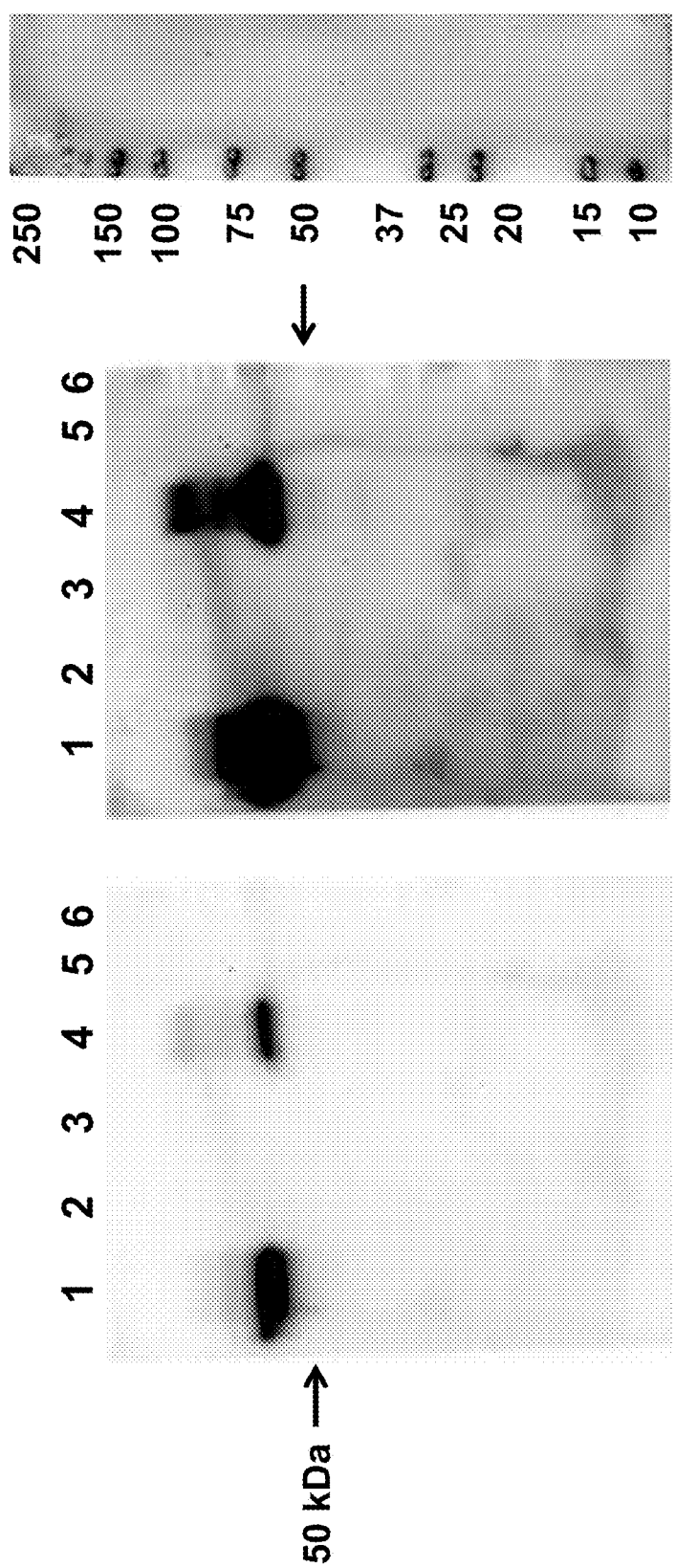
FIG. 1 is a pair of digital images illustrating the immunodetection analysis of the binding specificity of a mouse anti-MRSA-specific antibody to cellular proteins derived from *Staphylococcus aureus*. Sample loading of a 12% SDS-PAGE gel: 1: MR1 (15 μL/each lane); 2: MS1 (15 μL/each lane); 3: *E. coli* (15 μL/each lane); 4: MR2 (15 μL/each lane); 5: MS2 (15 μL/each lane); 6: Protein size markers. MR1 and MR2 are proteins derived from MRSA strains, MS1 and MS2 are derived from MSSA strains.
Figure 2B:
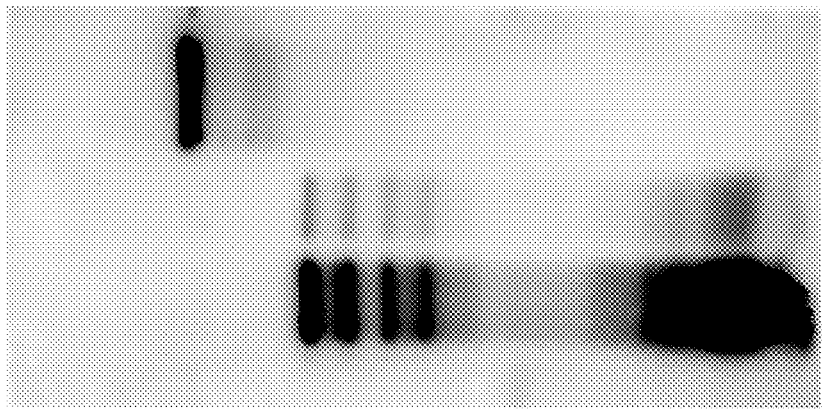
FIGS. 2A and 2B is a pair of digital images illustrating that monoclonal antibodies 4B10.B6 and 10A10.F2 both can bind to the MRSA PBP2a protein.
Figure 2A:
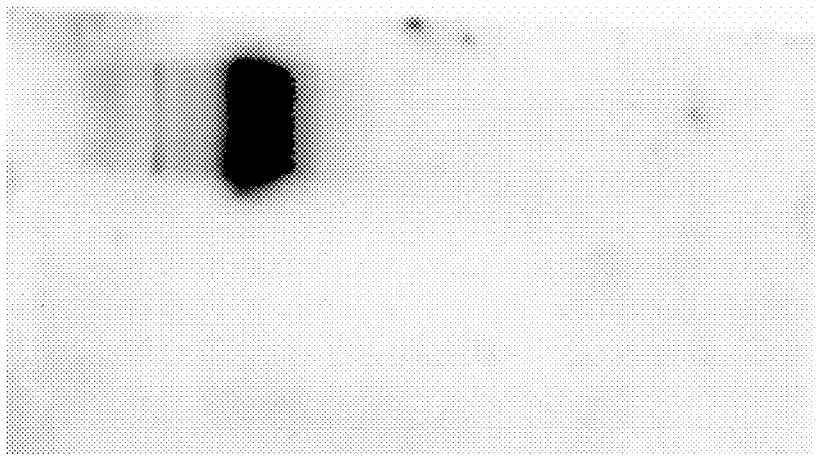
Figure 3:
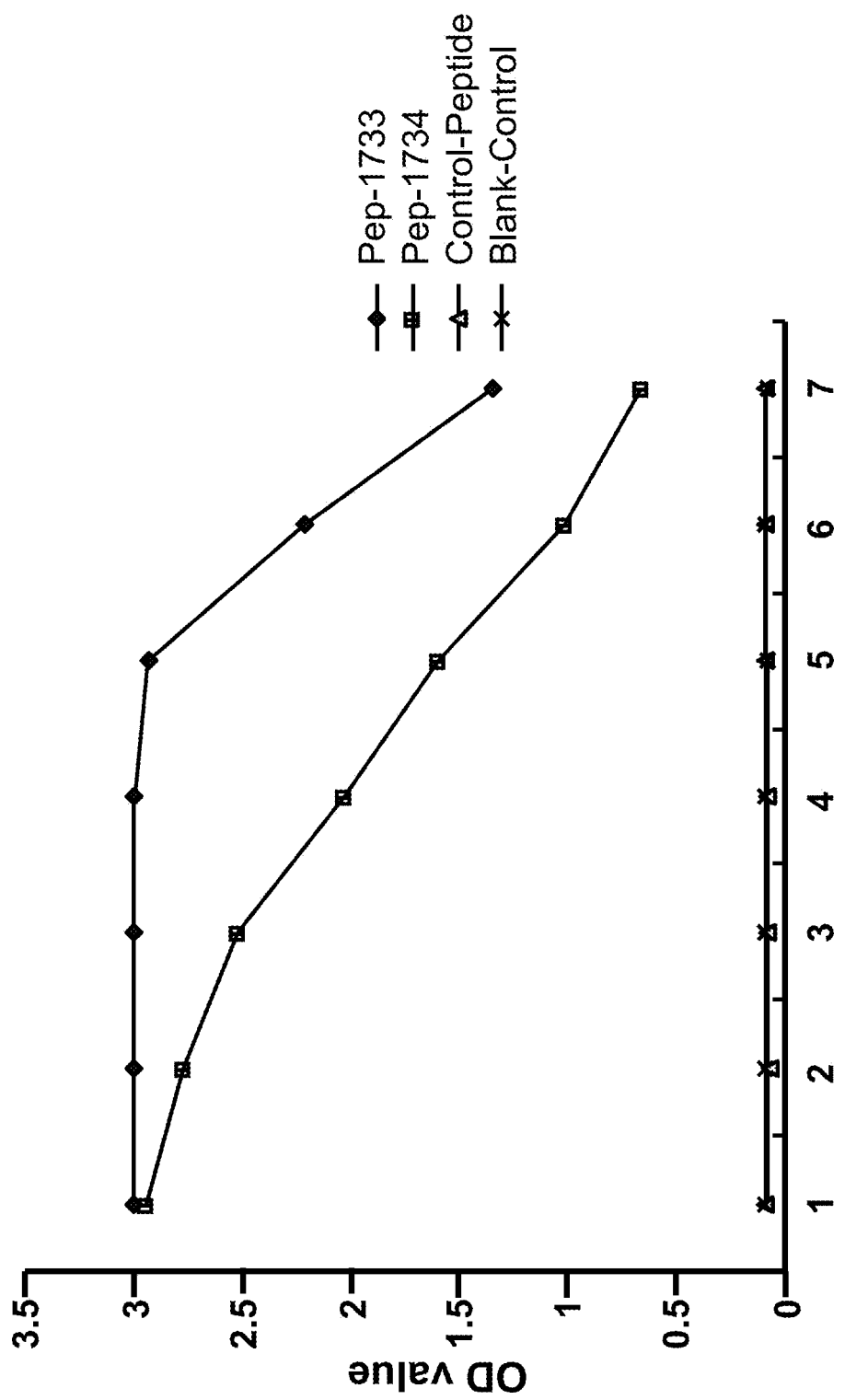
FIG. 3 shows a graph illustrating monoclonal antibody 4B10.B6 binding to synthetic peptide immunogens designated as 1733 (SEQ ID No.: 12) and 1734 (SEQ ID No.: 7), respectively. Coating antigens were at 100 ng/well, and unrelated-peptides as controls were introduced into a 96 well plate overnight at 4° C., then blocked with blocking buffer for 1 hr. Primary antibody was added at series dilution, and then detected by HRP-conjugated anti-mouse secondary antibody (1:20,000).
Figure 4A:
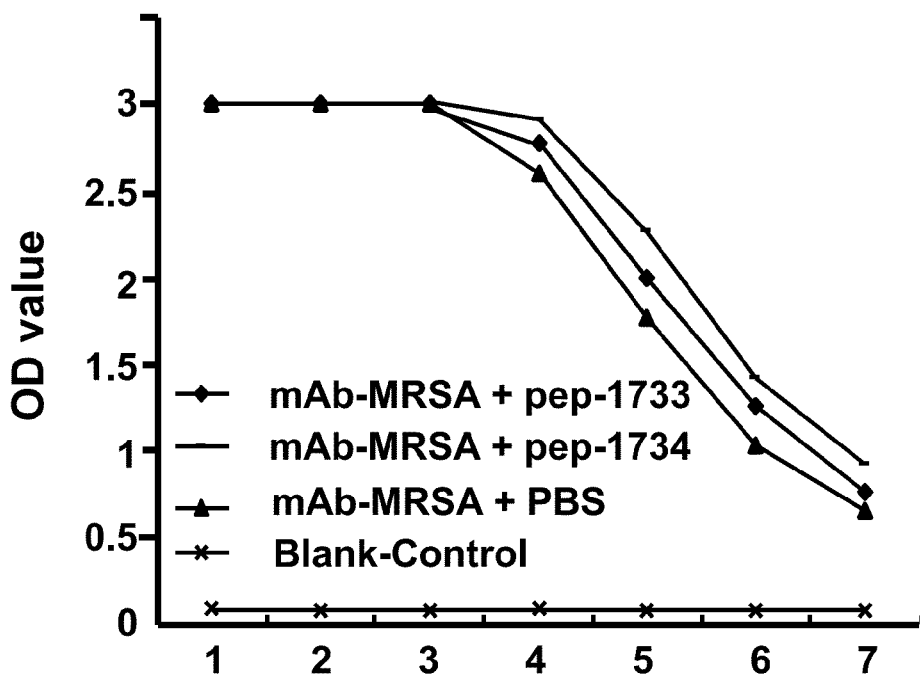
FIGS. 4A and 4B show a pair of graphs illustrating that binding of the monoclonal antibodies to the peptides 1733 and 1734 can be blocked in competition ELISA. Coated antigens were at 100 ng/well, and unrelated-peptides as controls were introduced into a 96 well plate overnight at 4° C., then blocked with blocking buffer for 1 hr. Primary antibody was added at series dilution, and then detected by HRP-conjugated anti-mouse secondary antibody (1:20,000).
Figure 4B:
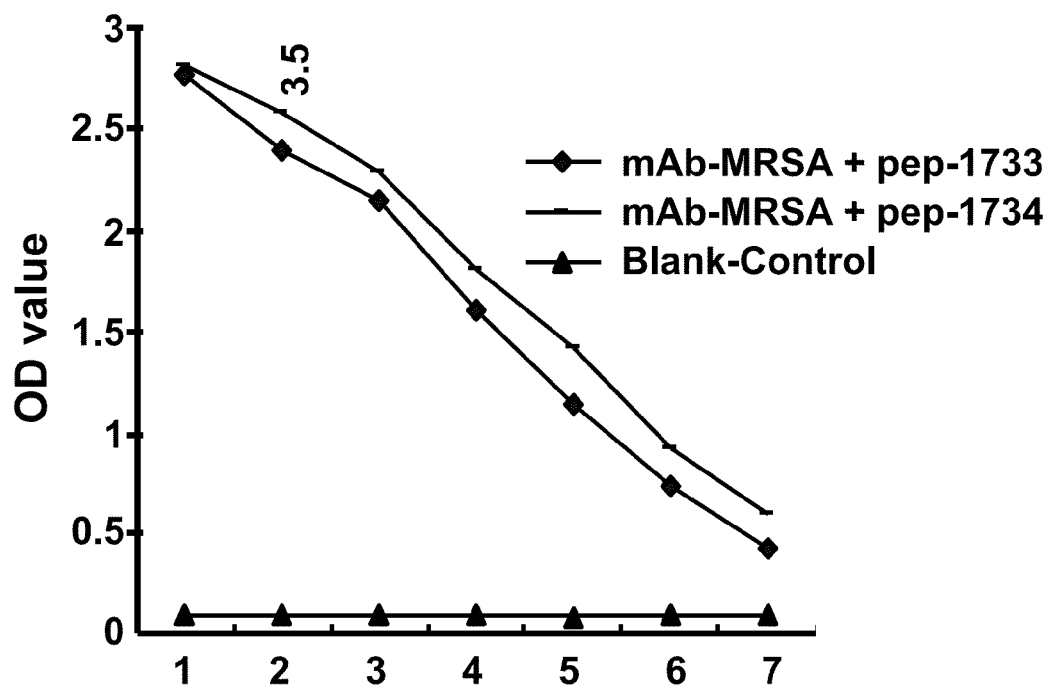
Figure 5:
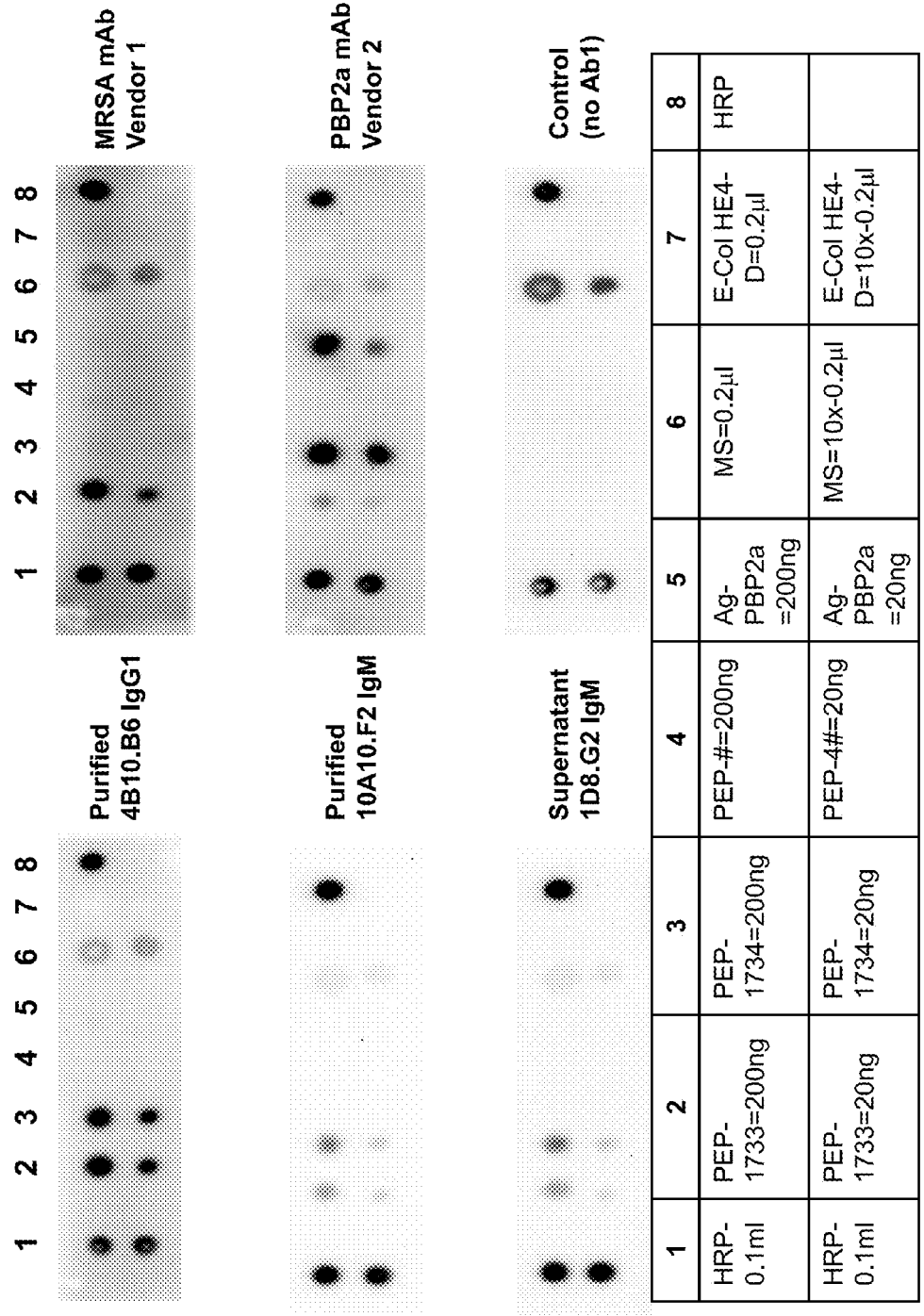
FIG. 5 illustrates the comparative binding of selected antibodies in dot blot analyses. The two purified mAbs of the disclosure can be bound to immunogens 1733 and 1734. A commercially available MRSA-specific monoclonal antibody bound only to immunogen 1733. A commercially available anti-PBP2a monoclonal antibody bound to immunogen 1734 as well as whole expressed protein.
Figure 6A:
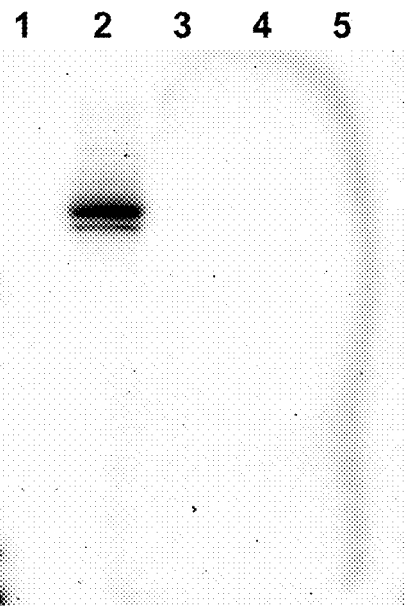
FIGS. 6A-6D are a series of digital images that illustrate the binding of the antibodies to the target in Western Blot analyses.
Figure 6B:
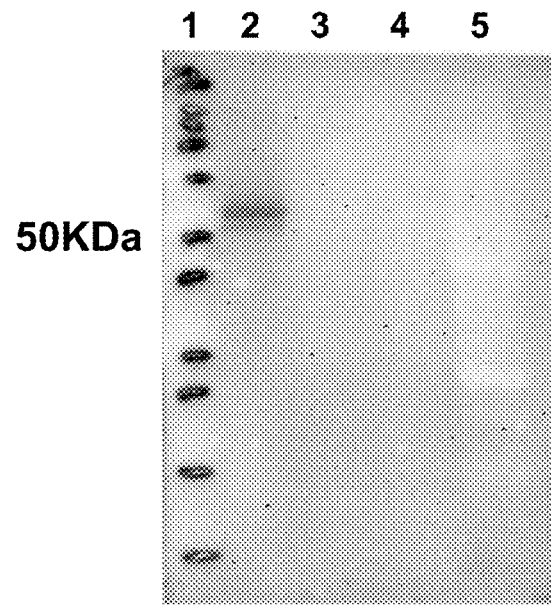
Figure 6C:
Figure 6D:
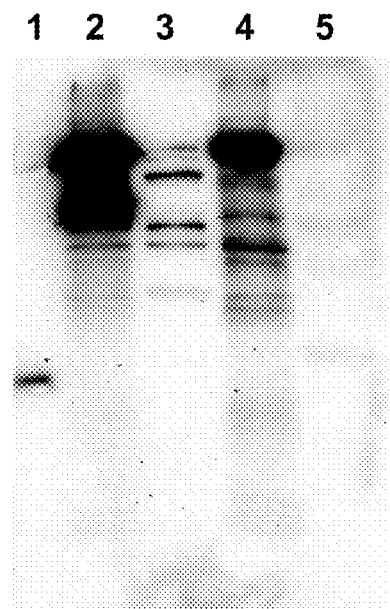
Figure 7B:
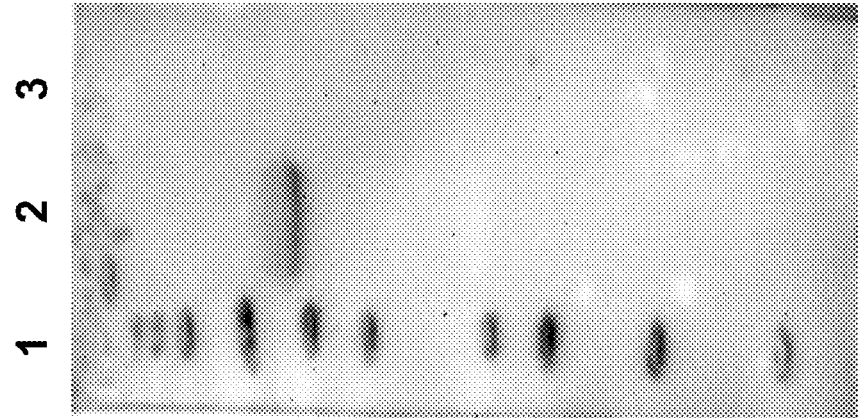
FIGS. 7A and 7B illustrate that the monoclonal antibodies of the disclosure were able to selectively precipitate the protein from MRSA lysate samples.
Figure 7A:
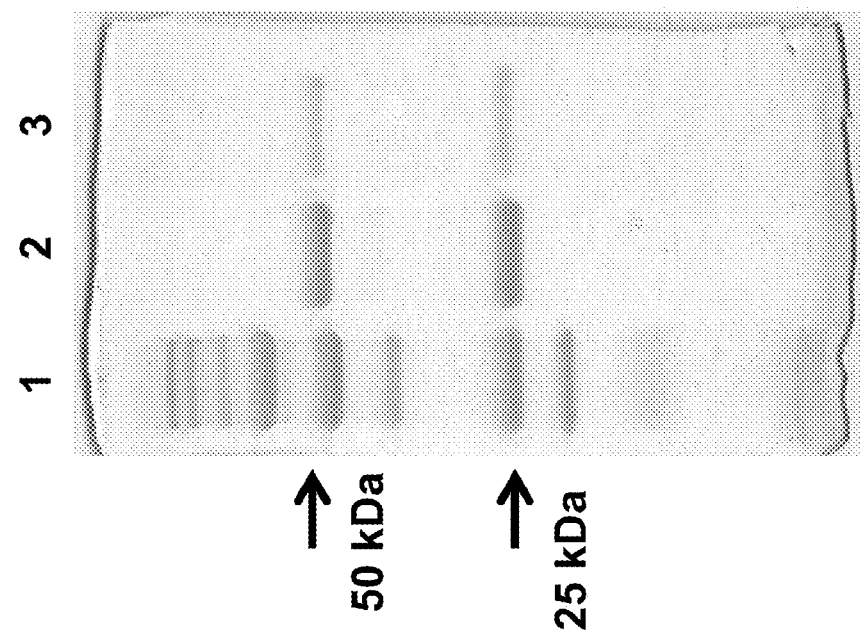

The drawings are described in greater detail in the description and examples below.

The details of some exemplary embodiments of the methods and systems of the present disclosure are set forth in the description below. Other features, objects, and advantages of the disclosure will be apparent to one of skill in the art upon examination of the following description, drawings, examples and claims. It is intended that all such additional systems, methods, features, and advantages be included within this description, be within the scope of the present disclosure, and be protected by the accompanying claims.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise.

Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. patent law and can mean " includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. patent law and the term is open-ended, allowing for the presence of more than that which is recited so long as basic or novel characteristics of that which is recited is not changed by the presence of more than that which is recited, but excludes prior art embodiments.

Prior to describing the various embodiments, the following definitions are provided and should be used unless otherwise indicated.

Definitions

In describing and claiming the disclosed subject matter, the following terminology will be used in accordance with the definitions set forth below.

The term "specific binding" as used herein refers to the specific recognition of one molecule, of two different molecules, compared to substantially less recognition of other molecules. Generally, the molecules have areas on their surfaces or in cavities giving rise to specific recognition between the two molecules. Exemplary of specific binding are antibody-antigen interactions, enzyme-substrate interactions, polynucleotide interactions, and so forth.

The term "antibody" as used herein refers to an immunoglobulin which specifically binds to and is thereby defined as complementary with a particular spatial and polar organization of another molecule. The antibody can be monoclonal, polyclonal, or a recombinant antibody, and can be prepared by techniques that are well known in the art such as immunization of a host and collection of sera (polyclonal) or by preparing continuous hybrid cell lines and collecting the secreted protein (monoclonal), or by cloning and expressing nucleotide sequences, or mutagenized versions thereof, coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM, IgY, etc. Fragments thereof may include Fab, Fv and $F(ab')_2$, Fab', scFv, and the like. In addition, aggregates, polymers, and conjugates of immunoglobulins or their fragments can be used where appropriate so long as binding affinity for a particular molecule is maintained.

The term "polyclonal antibody" as used herein refers to a heterogeneous mixture of antibodies that recognize and bind to different epitopes on the same antigen. Polyclonal antibodies may be obtained from crude serum preparations or may be purified using, for example, antigen affinity chromatography, Protein A/Protein G affinity chromatography, and the like.

The term "monoclonal antibody" as used herein refers to an antibody produced by a single hybridoma (or clone thereof) or other cell line, or by a transgenic mammal such that the monoclonal antibody will typically recognize one epitope on the antigen. The term "monoclonal" is not limited to any particular method for making the antibody, nor is the term limited to antibodies produced in a particular species, e.g., mouse, rat, etc.

Monoclonal antibodies directed toward an epitope specific to the PBP2a polypeptide of a methicillin-resistant strain of *S. aureus* can be produced using, for example but without limitation, the traditional "hybridoma" method or the newer "phage display" technique. For example, monoclonal antibodies of the disclosure may be made by the hybridoma method as described in Kohler et al., (1975) *Nature* 256:495; the human B-cell hybridoma technique (Kosbor et al., (1983) *Immunol. Today* 4:72; Cote et al., (1983) *Proc. Natl. Acad. Sci. U.S.A.* 80: 2026-2030; Brodeur et al., (1987) Monoclonal Antibody Production Techniques and Applications, pp. 51-63, Marcel Dekker, Inc., New York, and the EBV-hybridoma technique (Cole et al., (1985) Monoclonal Antibodies and Cancer Therapy, Alan R Liss Inc., New York N.Y., pp 77-96). Also provided by the disclosure are hybridoma cell lines that produce the monoclonal antibodies of the disclosure reactive with an epitope specific to the PBP2a polypeptide of a methicillin-resistant strain of *S. aureus*.

When the hybridoma technique is employed, myeloma cell lines can be used. Such cell lines suited for use in hybridoma-producing fusion procedures preferably are non-antibody-producing, have high fusion efficiency, and enzyme deficiencies that render them incapable of growing in certain selective media which support the growth of only the desired fused cells (hybridomas). For example, cell lines used in mouse fusions can be, but are not limited to, Sp-20, P3-X63/Ag8, P3-X63-Ag8.653, NS1/1.Ag 4 1, Sp210-Ag14, FO, NSO/U, MPC-11, MPC11-X45-GTG 1.7 and 5194/5XX0 Bul; cell lines used in rat fusions are R210.RCY3, Y3-Ag 1.2.3, IR983F and 4B210. Other cell lines useful for cell fusions are U-266, GM1500-GRG2, LICR-LON-HMy2 and UC729-6.

The term "epitope" as used herein refers to that portion of any molecule capable of being recognized by and bound by a specific antibody, at one or more of the binding agent's antigen binding regions. Epitopes usually consist of chemically active surface groupings of molecules, such as for example, amino acids or carbohydrate side chains, and have specific three-dimensional structural characteristics as well as specific charge characteristics. Epitopes as used herein may be contiguous or non-contiguous. Moreover, epitopes may be mimetic in that they comprise a three dimensional structure that is identical to the epitope used to generate the antibody, yet comprise none or only some of the amino acid residues found in the polypeptide used to stimulate an initial antibody immune response.

The terms "specific", "specifically", or "specificity" as used herein refer to the recognition, contact and formation of a stable complex between a molecule and another, together with substantially less to no recognition, contact and formation of a stable complex between the molecule and other molecules. Exemplary specific bindings are antibody-antigen interaction, cellular receptor-ligand interactions, polynucleotide hybridization, enzyme substrate interactions, etc. The term "specific" as used herein with reference to a molecular component of a complex, refers to the unique association of that component to the specific complex which the component is part of. The term "specific" as used herein with reference to a sequence of a polynucleotide refers to the unique association of the sequence with a single polynucleotide which is the complementary sequence.

The term "isolated" as used herein can refer to an epitope that is free from other elements that may be found in its natural environment, and preferably substantially free from any other contaminating mammalian amino acid sequences.

The monoclonal antibodies of the present invention are useful for the detection of MRSA infections in an animal or human subject, allowing a medical attendant to more usefully select a course of treatment, including the appropriate choice of an antibiotic, to reduce or eliminate the infection. Diagnostic assays for MRSA according to the disclosure can include, but are not limited to, methods utilizing a specific binding agent such as monoclonal antibodies 461066, 10A10F2, or 20G10H8 and a label to detect an MRSA-specific epitope in a body fluid, extract of cells or tissues, or a bacterial culture. The monoclonal antibodies, or fragments thereof, of the present disclosure can be used with or without modification. In an advantageous assay, the monoclonal antibody(ies) can be labeled by attaching, for example, a label or a reporter molecule. A wide variety of labels and reporter molecules are known in the art.

A variety of protocols for detecting a specific epitope using monoclonal antibodies specific for an epitope are known in the art. Examples include enzyme-linked immunosorbent assay (ELISA), radioimmunoassay (RIA) and Western blot analysis. A two-site, monoclonal-based immunoassay utilizing monoclonal antibodies reactive to two non-interfering epitopes such as are specifically bound by monoclonal antibody 4B10B6 of the disclosure, but a competitive binding assay can be employed. These assays are described, for example, in Maddox et al., (1983) *J. Exp. Med.* 158:1211.

In certain embodiments, monoclonal antibodies agents may be labeled with a detectable moiety. The detectable moiety can be any one that is capable of producing, either directly or indirectly, a detectable signal. For example, the detectable moiety may be a radioisotope, such as $^{3}$H, $^{14}$C, $^{32}$P, $^{35}$S, or $^{125}$I, a fluorescent or chemiluminescent compound, such as fluorescein isothiocyanate, rhodamine, or luciferin; or an enzyme, such as alkaline phosphatase, β-galactosidase, or horseradish peroxidase (Bayer et al., (1990) *Meth. Enz.* 184: 138-163).

The term "sandwich" assay" as used herein refers to an immunological binding assay of the non-competitive type. These assays have an amount of captured analyte that can be directly measured, such as, but not limited to, a polypeptide, a peptide, a mixture of polypeptides or peptide fragments thereof derived from a culture or isolate of a bacterial population suspected of comprising an MRSA strain of *S. aureus*. For example, in one embodiment, the capture agent is an antibody that can be bound directly to a solid substrate where it is immobilized. These immobilized antibodies then capture (bind to) an epitope present in the test sample. The analyte moiety thus immobilized is then bound to a labeling agent, such as a second antibody having a label.

It is contemplated, therefore, in a sandwich assay of the disclosure the target analyte may be derived from a biological sample suspected of comprising an MRSA strain. Any method known to one of skill in the art may be employed to disrupt bacterial cells of the biological sample. It is contemplated that the biological sample may be initially used as an inoculum to culture bacterial population s in the sample before breaking the cells and obtaining a lysate of the cells. The monoclonal antibodies of the disclosure may be bound to a solid support and then contacted with the bacterial lysate under conditions allowing specific binding of the bound monoclonal antibody(ies) to their specific epitope if present in the lysate. Another antibody that can be detectably labeled is then contacted to the bound analyte, specifically binding thereto. Detection of the bound label indicates the presence in the analyte, and hence in the biological sample of a population of MRSA. In another "sandwich" assay, the second antibody can lack a label, but can be bound by a labeled antibody specific for antibodies of the species from which the second antibody is derived. The second antibody also can be modified with a detectable moiety, such as biotin, to which a third labeled molecule can specifically bind, such as streptavidin. (See, for example, Harlow & Lane, Antibodies, A Laboratory Manual, Ch 14, Cold Spring Harbor Laboratory, NY (1988), incorporated herein by reference).

The present invention also provides Western blot methods to detect or quantify the presence of an MRSA-specific epitope in a biological sample. The technique generally comprises separating sample proteins by gel electrophoresis on the basis of molecular weight and transferring the proteins to a suitable solid support, such as nitrocellulose filter, a nylon filter, or derivatized nylon filter. The sample is incubated with a monoclonal antibody according to the disclosure that can specifically bind an epitope of the PBP2a polypeptide of MRSA strains and the resulting complex is detected. These antibodies may be directly labeled or alternatively may be subsequently detected using labeled antibodies that specifically bind to the antibody.

The terms "label" and "labeled molecule" as used herein as a component of a complex or molecule refer to a molecule capable of detection including, but not limited to, radioactive isotopes, fluorophores, chemoluminescent dyes, chromophores, enzymes, enzymes substrates, enzyme cofactors, enzyme inhibitors, dyes, metal ions, nanoparticles, metal sols, ligands (such as biotin, avidin, streptavidin or haptens) and the like. The term "fluorophore" refers to a substance or a portion thereof which is capable of exhibiting fluorescence in a detectable image. As a consequence, the term "labeling signal" as used herein refers to the signal emitted from the label that allows detection of the label, including but not limited to, fluorescence, chemolumiescence, production of a compound in outcome of an enzymatic reaction and the likes.

By "detectably labeled" is meant that a biotin-binding polypeptide or a fragment thereof, contains a moiety that is radioactive, or that is substituted with a fluorophore, or that is substituted with some other molecular species that elicits a physical or chemical response that can be observed or detected by the naked eye or by means of instrumentation such as, without limitation, scintillation counters, colorimeters, UV spectrophotometers and the like.

The term "detectable moiety" as used herein refers to various labeling moieties known in the art. Said moiety may be, for example, a radiolabel (e.g., $^3$H, $^{125}$I, $^{35}$S, $^{14}$C, $^{32}$P, etc.), detectable enzyme (e.g., horse radish peroxidase (HRP), alkaline phosphatase etc.), a dye, a colorimetric label such as colloidal gold or colored glass or plastic (e.g., polystyrene, polypropylene, latex, etc.), beads, or any other moiety capable of generating a detectable signal such as a colorimetric, fluorescent, chemiluminescent or electrochemiluminescent (ECL) signal.

The term "dye" as used herein refers to any reporter group whose presence can be detected by its light absorbing or light emitting properties. For example, Cy5 is a reactive water-soluble fluorescent dye of the cyanine dye family. Cy5 is fluorescent in the red region (about 650 to about 670 nm). It may be synthesized with reactive groups on either one or both of the nitrogen side chains so that they can be chemically linked to either nucleic acids or protein molecules. Labeling is done for visualization and quantification purposes. Cy5 is excited maximally at about 649 nm and emits maximally at about 670 nm, in the far red part of the spectrum; quantum yield is 0.28. FW=792. Suitable fluorophores(chromes) for the probes of the disclosure may be selected from, but not intended to be limited to, fluorescein isothiocyanate (FITC, green), cyanine dyes Cy2, Cy3, Cy3.5, Cy5, Cy5.5 Cy7, Cy7.5 (ranging from green to near-infrared), Texas Red, and the like. Derivatives of these dyes for use in the embodiments of the disclosure may be, but are not limited to, Cy dyes (Amersham Bioscience), Alexa Fluors (Molecular Probes Inc.,), HILYTE™ Fluors (AnaSpec), and DYLITE™ Fluors (Pierce, Inc).

The term "fluorescence" as used herein refers to a luminescence that is mostly found as an optical phenomenon in cold bodies, in which the molecular absorption of a photon triggers the emission of a photon with a longer (less energetic) wavelength. The energy difference between the absorbed and emitted photons ends up as molecular rotations, vibrations or heat. Sometimes the absorbed photon is in the ultraviolet range, and the emitted light is in the visible range, but this depends on the absorbance curve and Stokes shift of the particular fluorophore.

Spectroscopic, photochemical, biochemical, immunochemical, electrical, optical or chemical means can be used to detect such labels. The detection device and method may include, but is not limited to, optical imaging, electronic imaging, imaging with a CCD camera, integrated optical imaging, and mass spectrometry. Further, the amount of labeled or unlabeled probe bound to the target may be quantified. Such quantification may include statistical analysis.

Description

Mouse monoclonal antibodies, individually designated as 4B10.B6, 10A10.F2 and 20G10H8, each specifically recognizing the Penicillin Binding Protein 2a (PBP2a) derived from a strain of Methicillin-Resistant *Staphylococcus aureus* (MRSA) were produced and characterized by techniques well known to those in the art. The immunogen used to generate an immune response in a mouse was a PBP2a recombinant protein derived from a strain of Methicillin-Resistant *Staphylococcus aureus* (MRSA). The antibodies of the disclosure were produced from hybridomas resulting from the fusion of a mouse myeloma with B cells from the mouse immunized with the immunogen. The hybridoma producing the monoclonal antibody 4B10B6, designated hybridoma 4B10B6, has been deposited with the American Type Culture Collection, Manassas, Virginia, U.S.A. on Aug. 16, 2011, and given the ATCC Patent Deposit Designation PTA-12026. The hybridoma producing the monoclonal antibody 20G10H8, designated hybridoma 20G10H8, has been deposited with the American Type Culture Collection, Manassas, Virginia, U.S.A. on Aug. 16, 2011, and given the ATCC Patent Deposit Designation PTA-12027.

The IgM fraction comprising the monoclonal antibody 10A10.F2, of the tissue culture supernatant was purified by affinity chromatography.

The binding specificities of the monoclonal antibodies specific for native PBP2a from MRSA strains were assayed by ELISA, Western Blotting and immunoprecipitation (IP). The monoclonal antibodies of the disclosure do not bind to any protein isolated from Methicillin-Sensitive *Staphylococcus aureus* (MSSA) strains, as shown, for example, in FIG. 1.

The data showed that both monoclonal antibodies of the disclosure were able to distinguish MRSA from MSSA bacteria. The monoclonal antibodies have distinct recognition patterns for the regions of the PBP2a protein sequence (shown in FIGS. 8 and 9). Epitope mapping (as shown in FIG. 8) has localized regions of the PBP2a protein specifically recognized by one or both of the monoclonal antibodies. Accordingly, monoclonal antibodies designated as 20G10H8 and 10A10.F2 specifically recognize the amino acid region between about the amino acid position 27 to about position 46 of the PBP2a protein, and monoclonal antibody 4B10.B6 recognizes both this position and also that located between the amino acid positions of about 375 to about 400 of the PBP2a amino acid sequence according to SEQ ID No.: 14. Within these two regions, there is a sub-motif having the amino acid sequence EDK that it is contemplated constitutes the epitope or a region of the epitope specifically recognized by monoclonal antibody 4B10.B6. Without being bound by any one theory, the monoclonal antibodies may be sterically inhibited from recognizing and specifically binding to the epitope located amino acid positions of about 375 to about 400 of the PBP2a amino acid sequence according to SEQ ID No.: 14.

Thus, IgG1 monoclonal antibody 4B10.B6 has a unique binding profile, as compared with commercial available MRSA antibodies, in that it is capable of specifically recognizing synthetic peptides from both mapping ranges. Accordingly, it is considered likely that there are two regions in PBP2a acting as epitopes of sufficient structural similarity to be recognized by the one monoclonal. It is contemplated, therefore, that the monoclonal antibodies of the present disclosure having the ability to distinguish between MRSA and MSSA strains can be useful as the basis for a diagnostic assay useful in the clinical setting for determining whether and which antibiotics to administer to a patient.

Accordingly, the present disclosure encompasses embodiments of hybridomas and monoclonal antibodies generated from said hybridoma, the monoclonal antibody being specific for a region or regions of the bacterial protein PBP2a. Furthermore, the monoclonal antibodies of the present disclosure are able to distinguish strains of Staphylococcus aureus that are methicillin resistant from strains that are methicillin sensitive. The present disclosure further encompasses embodiments of a method of identifying strains of Staphylococcus aureus that are methicillin resistant from strains that are methicillin sensitive.

A variety of assay methods are known in the art that may usefully employ the monoclonal antibodies of the disclosure for the specific detection of MRSA strains. An especially useful method is a "sandwich assay" that can detect and identify epitopes of the PBP2a polypeptide found in MRSA strains. In this assay, the substrate-bound "capture" antibody can be either monoclonal antibodies designated as 4B10B6 (ATCC Patent Deposit Designation PTA-12026) combined with and 20G10H8 (ATCC Patent Deposit Designation PTA-12027) or monoclonal antibody 20G10H8 alone. A detectably labeled polyclonal antibody was used to then detect the bound epitope, as shown, for example, in Table 1.

One aspect of the disclosure encompasses embodiments of a monoclonal antibody characterized as specifically binding to an epitope of a methicillin-resistant strain of Staphylococcus aureus and not binding to an epitope of a methicillin-sensitive strain of Staphylococcus aureus.

In the embodiments of this aspect of the disclosure, the monoclonal antibody of is characterized as selectively binding to at least one epitope of a S. aureus PBP2a protein having the amino acid sequence SEQ ID No.: 14.

In the embodiments of this aspect of the disclosure, the monoclonal antibody of is characterized as selectively binding to an epitope located in a region between amino acid positions of about 27 to about 46 of the PBP2a protein sequence SEQ ID No.: 14 that consists essentially of the amino acid sequence DKEINNTIDAIEDKNFKQVY (SEQ ID No.: 1).

In the embodiments of this aspect of the disclosure, the monoclonal antibody of is characterized as selectively binding to an epitope located in a region between amino acid positions of about 27 to about 46 of the PBP2a protein sequence SEQ ID No.: 14 that consists essentially of the amino acid sequence DKEINNTIDAIEDKNFKQVY (SEQ ID No.: 1) and as selectively binding to an epitope located in a, the region between amino acid positions of about 375 to about 400 of the PBP2a protein sequence SEQ ID No.: 14 that consists essentially of the amino acid sequence SNEEYNKLTEDKKEPLLNKFQITTS (SEQ ID No.: 2).

In the embodiments of this aspect of the disclosure, the monoclonal antibody can have the designation 10A10.F2.

In the embodiments of this aspect of the disclosure, the monoclonal antibody can have the designation 4B10.B6 and is produced by the hybridoma deposited with the American Type Culture Collection and having the ATCC Patent Deposit Designation PTA-12026.

In the embodiments of this aspect of the disclosure, the monoclonal antibody can have the designation 20G10H8 and is produced by the hybridoma deposited with the American Type Culture Collection and having the ATCC Patent Deposit Designation PTA-12027.

Another aspect of the disclosure encompasses embodiments of an epitope of a PBP2a protein isolated from a methicillin-resistant strain of Staphylococcus aureus, where the epitope can selectively react with a monoclonal antibody characterized as distinguishing a methicillin-resistant strain of Staphylococcus aureus from a methicillin-sensitive strain of Staphylococcus aureus.

In the embodiments of this aspect of the disclosure, the epitope can be isolated from between the amino acid positions of about 27 to about 46 and having the amino acid sequence DKEINNTIDAIEDKNFKQVY (SEQ ID No.: 1), or between amino acid positions of about 375 to about 400 and having the amino acid sequence SNEEYNKLTEDKKEPLLNKFQITTS (SEQ ID No.: 2) of the S. aureus PBP2a protein, and wherein the epitope comprises the amino acid motif EDK In the embodiments of this aspect of the disclosure, the epitope can be specifically recognized by the monoclonal antibody 4B10.B6 produced by the hybridoma deposited with the American Type Culture Collection and having the ATCC Patent Deposit Designation PTA-12026.

In the embodiments of this aspect of the disclosure, the epitope can be specifically recognized by monoclonal antibody 10A10.F2.

In the embodiments of this aspect of the disclosure, the epitope can be specifically recognized by monoclonal antibody 20G10H8 produced by the hybridoma deposited with the American Type Culture Collection and having the ATCC Patent Deposit Designation PTA-12027.

Yet another aspect of the present disclosure encompasses embodiments of a method of differentiating a methicillin-resistant strain of Staphylococcus aureus from a methicillin-sensitive strain of Staphylococcus aureus, comprising the steps of: (i) obtaining a biological sample suspected of comprising a strain of Staphylococcus; (ii) providing a detection system by contacting the biological sample with at least one capture monoclonal antibody characterized as having specific affinity for an epitope of a PBP2a protein isolated from a methicillin-resistant strain of Staphylococcus aureus, wherein the monoclonal antibody is further characterized as distinguishing a methicillin-resistant strain of Staphylococcus aureus from a methicillin-sensitive strain of Staphylococcus aureus; and (iii) detecting the binding of the at least one capture monoclonal antibody to the biological sample, thereby detecting a population of methicillin-resistant S. aureus in the biological sample.

In the embodiments of this aspect of the disclosure, the at least one capture monoclonal antibody can be bound to a solid support.

In the embodiments of this aspect of the disclosure, the at least one capture monoclonal antibody can be selected from the group consisting of the monoclonal antibodies designated: 4B10.B6 having the ATCC Patent Deposit Designation PTA-12026, 10A10.F2, and 20G10H8 having the ATCC Patent Deposit Designation PTA-12027.

In the embodiments of this aspect of the disclosure, the at least one capture monoclonal antibody can be antibody 4B10.B6 having the ATCC Patent Deposit Designation PTA-12026.

In the embodiments of this aspect of the disclosure, the at least one capture monoclonal antibody can be antibody 10A10.F2.

In the embodiments of this aspect of the disclosure, the at least one capture monoclonal antibody is antibody 20G10H8 having the ATCC Patent Deposit Designation PTA-12027.

In the embodiments of this aspect of the disclosure, the at least one capture monoclonal antibody can be a combination of monoclonal antibody designated: 4B10.B6 having the ATCC Patent Deposit Designation PTA-12026 and monoclonal antibody 20G10H8 having the ATCC Patent Deposit Designation PTA-12027.

In the embodiments of this aspect of the disclosure, the step (iii) can comprise contacting the detection system with a second antibody, where the second antibody is detectably labeled and characterized as specifically binding to a PBP2a epitope bound to the at least one capture monoclonal antibody.

The specific examples below are to be construed as merely illustrative, and not imitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and the present disclosure and protected by the following claims.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20 ° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt. % to about 5 wt. %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified.

EXAMPLES

Example 1

A membrane blot, as shown in FIG. 1, was probed with purified mouse anti-MRSA primary antibody (2 μg/ml). Proteins were clearly visualized using in-house anti-mouse secondary antibody conjugated to HRP (1:5000) and chemiluminescence detection system. In FIG. 1, arrows indicate that the antibody specifically recognized target protein from bacterial samples.

Example 2

TABLE 1

Clinical sample detection using a PBP2a-specific sandwich ELISA system

| | Clinical samples | |
|---|---|---|
| | Beijing, China | USA |
| MRSA | 8 (10)[a] | 18 (19) |
| MSSA | 0 (10) | 1[b] (16) |

[a]number of samples showing in parentheses;
[b]false positive.

Based on the data in this table: Sensitivity: 90.1%; Specificity: 96.2%

We claim:

1. A method of differentiating a methicillin-resistant strain of *Staphylococcus aureus* from a methicillin-sensitive strain of *Staphylococcus aureus*, comprising the steps of:
   (i) obtaining a biological sample suspected of comprising a strain of *Staphylococcus*;
   (ii) providing a detection system by contacting the biological sample with at least one capture monoclonal antibody characterized as having specific affinity for an epitope of a PBP2a protein isolated from a methicillin-resistant strain of *Staphylococcus aureus*, wherein the monoclonal antibody is further characterized as distinguishing a methicillin-resistant strain of *Staphylococcus aureus* from a methicillin-sensitive strain of *Staphylococcus aureus*, wherein the at least one capture monoclonal antibody is selected from the group consisting of the monoclonal antibodies designated: 4B10.B6 produced by the hybridoma having the ATCC Patent Deposit Designation PTA-12026, and 20G10H8 produced by the hybridoma having the ATCC Patent Deposit Designation PTA-12027; and
   (iii) detecting the binding of the at least one capture monoclonal antibody to the biological sample, thereby detecting a population of methicillin-resistant *S. aureus* in the biological sample.

2. The method of claim 1, wherein the at least one capture monoclonal antibody is bound to a solid support.

3. The method of claim 1, wherein the at least one capture monoclonal antibody is antibody 4B10.B6 produced by the hybridoma having the ATCC Patent Deposit Designation PTA-12026.

4. The method of claim 1, wherein the at least one capture monoclonal antibody is antibody 20G10H8 produced by the hybridoma having the ATCC Patent Deposit Designation PTA-12027.

5. The method of claim 1, wherein the at least one capture monoclonal antibody is a combination of monoclonal antibody designated: 4B10.B6 produced by the hybridoma having the ATCC Patent Deposit Designation PTA-12026 and monoclonal antibody 20G10H8 produced by the hybridoma having the ATCC Patent Deposit Designation PTA-12027.

6. The method of claim 1, wherein the step (iii) comprises contacting the detection system with a second antibody, wherein the second antibody is detectably labeled and characterized as specifically binding to a PBP2a epitope bound to the at least one capture monoclonal antibody.

* * * * *

SEQUENCE LISTING

```
<160> NUMBER OF SEQ ID NOS: 14

<210> SEQ ID NO 1
<211> LENGTH: 20
<212> TYPE: PRT
<213> ORGANISM: Artificial sequence
<220> FEATURE:
<223> OTHER INFORMATION: PBP2a protein amino acids 27-46

<400> SEQUENCE: 1

Asp Lys Glu Ile Asn Asn Thr Ile Asp Ala Ile Glu Asp Lys Asn Phe
1               5                   10                  15

Lys Gln Val Tyr
            20

<210> SEQ ID NO 2
<211> LENGTH: 25
<212> TYPE: PRT
<213> ORGANISM: Artificial sequence
<220> FEATURE:
<223> OTHER INFORMATION: PBP2a protein amino acids 375-400
```

```
-continued

<400> SEQUENCE: 2

Ser Asn Glu Glu Tyr Asn Lys Leu Thr Glu Asp Lys Lys Glu Pro Leu
1               5                   10                  15

Leu Asn Lys Phe Gln Ile Thr Thr Ser
            20                  25

<210> SEQ ID NO 3
<211> LENGTH: 20
<212> TYPE: PRT
<213> ORGANISM: Artificial sequence
<220> FEATURE:
<223> OTHER INFORMATION: PBP2a protein amino acids 1-20

<400> SEQUENCE: 3

Met Lys Lys Ile Lys Ile Val Pro Leu Ile Leu Ile Val Val Val Val
1               5                   10                  15

Gly Phe Gly Ile
            20

<210> SEQ ID NO 4
<211> LENGTH: 20
<212> TYPE: PRT
<213> ORGANISM: Artificial sequence
<220> FEATURE:
<223> OTHER INFORMATION: PBP2a protein amino acids 16-37

<400> SEQUENCE: 4

Val Gly Phe Gly Ile Tyr Phe Tyr Ala Ser Lys Asp Lys Glu Ile Asn
1               5                   10                  15

Asn Thr Ile Asp
            20

<210> SEQ ID NO 5
<211> LENGTH: 20
<212> TYPE: PRT
<213> ORGANISM: Artificial sequence
<220> FEATURE:
<223> OTHER INFORMATION: PBP2a protein amino acids 31-50

<400> SEQUENCE: 5

Asn Asn Thr Ile Asp Ala Ile Glu Asp Lys Asn Phe Lys Gln Val Tyr
1               5                   10                  15

Lys Asp Ser Ser
            20

<210> SEQ ID NO 6
<211> LENGTH: 20
<212> TYPE: PRT
<213> ORGANISM: Artificial sequence
<220> FEATURE:
<223> OTHER INFORMATION: PBP2a protein amino acids 46-65

<400> SEQUENCE: 6

Tyr Lys Asp Ser Ser Tyr Ile Ser Lys Ser Asp Asn Gly Glu Val Glu
1               5                   10                  15

Met Thr Glu Arg
            20

<210> SEQ ID NO 7
<211> LENGTH: 15
<212> TYPE: PRT
<213> ORGANISM: Artificial sequence
<220> FEATURE:
<223> OTHER INFORMATION: PBP2a protein amino acids 31-45 Antigen 1734
```

```
<400> SEQUENCE: 7

Asn Asn Thr Ile Asp Ala Ile Glu Asp Lys Asn Phe Lys Gln Val
1               5                   10                  15

<210> SEQ ID NO 8
<211> LENGTH: 20
<212> TYPE: PRT
<213> ORGANISM: Artificial sequence
<220> FEATURE:
<223> OTHER INFORMATION: PBP2a protein amino acids 361-380

<400> SEQUENCE: 8

Val Ser Thr Pro Ser Tyr Asp Val Tyr Pro Phe Met Tyr Gly Met Ser
1               5                   10                  15

Asn Glu Glu Tyr
            20

<210> SEQ ID NO 9
<211> LENGTH: 20
<212> TYPE: PRT
<213> ORGANISM: Artificial sequence
<220> FEATURE:
<223> OTHER INFORMATION: PBP2a protein amino acids 376-395

<400> SEQUENCE: 9

Ser Asn Glu Glu Tyr Asn Lys Leu Thr Glu Asp Lys Lys Glu Pro Leu
1               5                   10                  15

Leu Asn Lys Phe
            20

<210> SEQ ID NO 10
<211> LENGTH: 20
<212> TYPE: PRT
<213> ORGANISM: Artificial sequence
<220> FEATURE:
<223> OTHER INFORMATION: PBP2a protein amino acids 391-410

<400> SEQUENCE: 10

Leu Leu Asn Lys Phe Gln Ile Thr Thr Ser Pro Gly Ser Thr Gln Lys
1               5                   10                  15

Ile Leu Thr Ala
            20

<210> SEQ ID NO 11
<211> LENGTH: 20
<212> TYPE: PRT
<213> ORGANISM: Artificial sequence
<220> FEATURE:
<223> OTHER INFORMATION: PBP2a protein amino acids 406-425

<400> SEQUENCE: 11

Lys Ile Leu Thr Ala Met Ile Gly Leu Asn Asn Lys Thr Leu Asp Asp
1               5                   10                  15

Lys Thr Ser Tyr
            20

<210> SEQ ID NO 12
<211> LENGTH: 15
<212> TYPE: PRT
<213> ORGANISM: Artificial sequence
<220> FEATURE:
<223> OTHER INFORMATION: PBP2a protein amino acids 376-390
```

-continued

```
<400> SEQUENCE: 12

Ser Asn Glu Glu Tyr Asn Lys Leu Thr Glu Asp Lys Lys Glu Pro
1               5                   10                  15

<210> SEQ ID NO 13
<211> LENGTH: 10
<212> TYPE: PRT
<213> ORGANISM: Artificial sequence
<220> FEATURE:
<223> OTHER INFORMATION: PBP2a protein epitope-X is variable amino
      acid(s)
<220> FEATURE:
<221> NAME/KEY: misc_feature
<222> LOCATION: (2)..(2)
<223> OTHER INFORMATION: Xaa can be any naturally occurring amino
      acid
<220> FEATURE:
<221> NAME/KEY: misc_feature
<222> LOCATION: (4)..(4)
<223> OTHER INFORMATION: Xaa can be any naturally occurring amino
      acid
<220> FEATURE:
<221> NAME/KEY: misc_feature
<222> LOCATION: (8)..(8)
<223> OTHER INFORMATION: Xaa can be any naturally occurring amino
      acid
<220> FEATURE:
<221> NAME/KEY: misc_feature
<222> LOCATION: (10)..(10)
<223> OTHER INFORMATION: Xaa can be any naturally occurring amino
      acid

<400> SEQUENCE: 13

Asn Xaa Thr Xaa Glu Asp Lys Xaa Lys Xaa
1               5                   10

<210> SEQ ID NO 14
<211> LENGTH: 668
<212> TYPE: PRT
<213> ORGANISM: Staphylococcus aureus
<220> FEATURE:
<221> NAME/KEY: MISC_FEATURE
<222> LOCATION: (1)..(668)
<223> OTHER INFORMATION: PBP2a polypeptide

<400> SEQUENCE: 14

Met Lys Lys Ile Lys Ile Val Pro Leu Ile Leu Ile Val Val Val
1               5                   10                  15

Gly Phe Gly Ile Tyr Phe Tyr Ala Ser Lys Asp Lys Glu Ile Asn
                    20                  25                  30

Thr Ile Asp Ala Ile Glu Asp Lys Asn Phe Lys Gln Val Tyr Lys Asp
            35                  40                  45

Ser Ser Tyr Ile Ser Lys Ser Asp Asn Gly Glu Val Glu Met Thr Glu
    50                  55                  60

Arg Pro Ile Lys Ile Tyr Asn Ser Leu Gly Val Lys Asp Ile Asn Ile
65                  70                  75                  80

Gln Asp Arg Lys Ile Lys Lys Val Ser Lys Asn Lys Lys Arg Val Asp
                85                  90                  95

Ala Gln Tyr Lys Ile Lys Thr Asn Tyr Gly Asn Ile Asp Arg Asn Val
            100                 105                 110

Gln Phe Asn Phe Val Lys Glu Asp Gly Met Trp Lys Leu Asp Trp Asp
        115                 120                 125

His Ser Val Ile Ile Pro Gly Met Gln Lys Asp Gln Ser Ile His Ile
    130                 135                 140

Glu Asn Leu Lys Ser Glu Arg Gly Lys Ile Leu Asp Arg Asn Asn Val
145                 150                 155                 160
```

-continued

```
Glu Leu Ala Asn Thr Gly Thr Ala Tyr Glu Ile Gly Ile Val Pro Lys
                165                 170                 175

Asn Val Ser Lys Lys Asp Tyr Lys Ala Ile Ala Lys Glu Leu Ser Ile
            180                 185                 190

Ser Glu Asp Tyr Ile Lys Gln Gln Met Asp Gln Asn Trp Val Gln Asp
        195                 200                 205

Asp Thr Phe Val Pro Leu Lys Thr Val Lys Lys Met Asp Glu Tyr Leu
    210                 215                 220

Ser Asp Phe Ala Lys Lys Phe His Leu Thr Thr Asn Glu Thr Glu Ser
225                 230                 235                 240

Arg Asn Tyr Pro Leu Gly Lys Ala Thr Ser His Leu Leu Gly Tyr Val
                245                 250                 255

Gly Pro Ile Asn Ser Glu Glu Leu Lys Gln Lys Glu Tyr Lys Gly Tyr
            260                 265                 270

Lys Asp Asp Ala Val Ile Gly Lys Lys Gly Leu Glu Lys Leu Tyr Asp
        275                 280                 285

Lys Lys Leu Gln His Glu Asp Gly Tyr Arg Val Thr Ile Val Asp Asp
    290                 295                 300

Asn Ser Asn Thr Ile Ala His Thr Leu Ile Glu Lys Lys Lys Lys Asp
305                 310                 315                 320

Gly Lys Asp Ile Gln Leu Thr Ile Asp Ala Lys Val Gln Lys Ser Ile
                325                 330                 335

Tyr Asn Asn Met Lys Asn Asp Tyr Gly Ser Gly Thr Ala Ile His Pro
            340                 345                 350

Gln Thr Gly Glu Leu Leu Ala Leu Val Ser Thr Pro Ser Tyr Asp Val
        355                 360                 365

Tyr Pro Phe Met Tyr Gly Met Ser Asn Glu Glu Tyr Asn Lys Leu Thr
    370                 375                 380

Glu Asp Lys Lys Glu Pro Leu Leu Asn Lys Phe Gln Ile Thr Thr Ser
385                 390                 395                 400

Pro Gly Ser Thr Gln Lys Ile Leu Thr Ala Met Ile Gly Leu Asn Asn
                405                 410                 415

Lys Thr Leu Asp Asp Lys Thr Ser Tyr Lys Ile Asp Gly Lys Gly Trp
            420                 425                 430

Gln Lys Asp Lys Ser Trp Gly Gly Tyr Asn Val Thr Arg Tyr Glu Val
        435                 440                 445

Val Asn Gly Asn Ile Asp Leu Lys Gln Ala Ile Glu Ser Ser Asp Asn
    450                 455                 460

Ile Phe Phe Ala Arg Val Ala Leu Glu Leu Gly Ser Lys Lys Phe Glu
465                 470                 475                 480

Lys Gly Met Lys Lys Leu Gly Val Gly Glu Asp Ile Pro Ser Asp Tyr
                485                 490                 495

Pro Phe Tyr Asn Ala Gln Ile Ser Asn Lys Asn Leu Asp Asn Glu Ile
            500                 505                 510

Leu Leu Ala Asp Ser Gly Tyr Gly Gln Gly Glu Ile Leu Ile Asn Pro
        515                 520                 525

Val Gln Ile Leu Ser Ile Tyr Ser Ala Leu Glu Asn Asn Gly Asn Ile
    530                 535                 540

Asn Ala Pro His Leu Leu Lys Asp Thr Lys Asn Lys Val Trp Lys Lys
545                 550                 555                 560

Asn Ile Ile Ser Lys Glu Asn Ile Asn Leu Leu Thr Asp Gly Met Gln
                565                 570                 575

Gln Val Val Asn Lys Thr His Lys Glu Asp Ile Tyr Arg Ser Tyr Ala
            580                 585                 590
```

-continued

```
Asn Leu Ile Gly Lys Ser Gly Thr Ala Glu Leu Lys Met Lys Gln Gly
        595             600             605

Glu Thr Gly Arg Gln Ile Gly Trp Phe Ile Ser Tyr Asp Lys Asp Asn
    610             615             620

Pro Asn Met Met Met Ala Ile Asn Val Lys Asp Val Gln Asp Lys Gly
625             630             635             640

Met Ala Ser Tyr Asn Ala Lys Ile Ser Gly Lys Val Tyr Asp Glu Leu
                645             650             655

Tyr Glu Asn Gly Asn Lys Lys Tyr Asp Ile Asp Glu
            660             665
```